US006433019B1

(12) United States Patent
Nawa

(10) Patent No.: US 6,433,019 B1
(45) Date of Patent: Aug. 13, 2002

(54) NEUROTROPHIC FACTOR SECRETION PROMOTERS

(75) Inventor: Hiroyuki Nawa, Niigata (JP)

(73) Assignee: Sumitomo Pharmaceuticals Company, Limited, Osaka (JP)

(*) Notice: Subject to any disclaimer, the term of this patent is extended or adjusted under 35 U.S.C. 154(b) by 0 days.

(21) Appl. No.: 09/601,186

(22) PCT Filed: Jan. 27, 1999

(86) PCT No.: PCT/JP99/00340

§ 371 (c)(1),
(2), (4) Date: Jul. 28, 2000

(87) PCT Pub. No.: WO99/38539

PCT Pub. Date: Aug. 5, 1999

(30) Foreign Application Priority Data

Jan. 30, 1998 (JP) .......................................... 10-033757

(51) Int. Cl.⁷ .............................................. A61K 31/41
(52) U.S. Cl. ........................................ 514/632; 514/634
(58) Field of Search ................................... 514/632, 634

(56) References Cited

U.S. PATENT DOCUMENTS

| | | | |
|---|---|---|---|
| 5,447,939 A | * | 9/1995 | Glasky et al. |
| 5,508,045 A | * | 4/1996 | Harrison et al. |
| 5,800,385 A | * | 9/1998 | Demopulos et al. |
| 5,958,427 A | * | 9/1999 | Salzman et al. |
| 5,965,529 A | * | 10/1999 | Garfield et al. |
| 6,127,370 A | * | 10/2000 | Smith et al. |
| 6,133,320 A | * | 10/2000 | Yallampalli et al. |

FOREIGN PATENT DOCUMENTS

| | | |
|---|---|---|
| EP | 0446699 B1 | 9/1991 |
| WO | 9315779 A1 | 8/1993 |
| WO | WO-95/09636 A1 * | 4/1995 |
| WO | 9614842 A1 | 5/1996 |

OTHER PUBLICATIONS

Hindley et al., Journal of Neuroscience Research, vol. 47, pp. 427–439 (1997).
Clarris et al., Journal of Neuroscience Research, vol. 38, pp. 248–258 (1994).
Dyer et al., Peptides, Vo;. 16, No. 3, pp. 515–522 (1995).
Garg et al., European Journal of Pharmacology, vol. 237, pp. 243–249 (1993).
Solomon H. Snyder et al., Scientific American, May 1992, pp. 28–35.
Jane E. Haley et al., Neuron, vol. 8, Feb. 1992, pp. 211–216.
Erin M. Schuman et al., Ann. Rev. Neurosci., vol. 17, 1994, pp. 153–183.
Miwa Toyoda et al., Jpn. J. Pharmacol. vol. 71, 1996, pp. 205–211.
K. Yamada et al., Neuroscience, vol. 74, No. 2, 1996, pp. 365–374.
Sheldon Milstien et al., Journal of Neurochemistry, vol. 63, No. 3, 1994, pp. 1178–1180.
G. William Rebeck et al., Neuroscience Letters, vol. 152, 1993, pp. 165–168.

* cited by examiner

*Primary Examiner*—William R. A. Jarvis
*Assistant Examiner*—Vickie Kim
(74) *Attorney, Agent, or Firm*—Birch, Stewart, Kolasch & Birch, LLP

(57) ABSTRACT

The present invention relates to a neurotrophic factor secretagogue, in particular, to a BDNF (brain-derived neurotrophic factor) secretagogue, which comprises as an active ingredient an NO donor. The medicament of the present invention promotes the secretion of neurotrophic factors from mammalian central neural cells. Thus, the medicament of the present invention, i.e., NO donor, is possibly applicable to the treatment of diseases caused by neutrotrophic factors, for example, neurodegenerative diseases, and is expected to exhibit the efficacious effects thereon. Also, the present invention provides a novel medication for neurodegenerative diseases.

6 Claims, 3 Drawing Sheets

NEUROTROPHIC FACTOR SECRETION PROMOTERS

This application is the national phase under 35 U.S.C. §371 of PCT International Application No. PCT/JP99/00340 which has an International filing date of Jan. 27, 1999, which designated the United States of America.

TECHNICAL FIELD

The present invention relates to a neurotrophic factor secretagogue being useful in the treatment of neurodegenerative diseases, etc.

BACKGROUND ART

Nitric oxide (NO) is a free radical gas, which was found as an endogenous factor being produced by vascular endothelial cells, and it has been known to be involved with the regulation of vascular tone, platelet aggregation, neurotransmission mechanism and immune activation (Reference 1). It is reported that NO exhibits a neurotransmitter-like activity in the central nervous system, and is involved with the long term potentiation (LTP) and the learning memory (References 2, 3, 4 and 5).

However, the connection between NO and neurodegenerative diseases (Alzheimer's disease, Amyotrophic lateral sclerosis, etc.) has not been clarified yet. Although several studies have been done using some techniques such as component analysis of cerebrospinal fluid from patients (Reference 6) and histological analysis of brains (Reference 7), there is no decided indication as to the connection between the NO producing system in tissue and the pathogenesis of these diseases. Further, it is rather a common concept that the increase in NO amount in tissues is not useful in the treatment of neurodegenerative diseases. Recently, many patent applications have been filed as to technical ideas of treatment of neuro-degenerative diseases by administering an NO synthase inhibitor in order to reduce the NO production in neural cells (References 8 and 9), these patent applications are based on a hypothesis that NO may be toxic to neural cells, and the technical idea of the present invention is completely different from those of these patent applications.

Exceptionally, there is a patent application suggesting the treatment of central nervous diseases by NO synthesis acceleration (Reference 10), but the method thereof is that the NO concentration in blood is increased by ozone gas and ultraviolet irradiation by which platelet aggregation-related diseases, hypertension, depression, infections, and impotence are cured. Depression is not a neurodegenerative disease, nor is cured by a neurotrophic factor. Besides, said application never discloses or suggests the technical idea of the present invention that an NO donor being exogenously administered enhances the secretion of neurotrophic factors.

In addition, it is reported that Interleukin-1 (IL-1), Prostaglandin, Tumor Necrosis Factor (TNF), Fibroblast growth factor (FGF), etc. show activities of enhancing neurotrophic factor secretion, especially NGF, but it is not reported yet that an NO donor promotes the secretion of a neurotrophic factor, especially BDNF, in neural cells.

Reference 1: Snyder et al.: Scientific American, p. 28–35 (1992.5)
Reference 2: Haley, J. et al.: Neuron 8, 211–216 (1992)
Reference 3: Schuman, E. M. and Madison, D. V.: Ann. Rev. Neurosci. 17, 153–183 (1994)
Reference 4: Toyoda, M S et al.: Jpn. J. Pharmacol. 71, 205–211 (1996)
Reference 5: Yamada, K et al.: Neuroscience 74 (2), 365–374 (1996)
Reference 6: Milstein, S et al.: J. Neurochemistry 63 (3), 1178–1180 (1994)
Reference 7: Rebeck, G. W. et al.: Neuroscience letters 152, 165–168 (1993)
Reference 8: JP-A-4-270255 (EP 446699): Merrell Dow Pharmaceuticals Inc.
Reference 9: WO 96/14842: Merck & Co., Inc.
Reference 10: JP-A-7-503722 (WO 93/15779): Vasogen, Inc.

SUMMARY OF INVENTION

Neurotrophic factors such as BDNF are expected to exhibit pharmacological activities on neurodegenerative diseases, nerve damages by ischemia or injury, or moreover on optic nerve damages. These factors are inherently proteins expressed and secreted in the living body, and a lower molecular weight compound which can promote the secretion of these proteins is considered to be useful in the clinical field. An object of the present invention is to provide a medicament comprising as an active ingredient a lower molecular weight compound, and being capable of promoting the neurotrophic factor activities in the living body, that is, an agent for treatment of diseases being responsive to neurotrophic factors.

That is, the gist of the present invention is below.

[1] A neurotrophic factor secretagogue, which comprises as an active ingredient an NO donor.
[2] The neurotrophic factor secretagogue according to the above [1], wherein the NO donor is a spontaneous NO donor.
[3] The neurotrophic factor secretagogue according to the above [1], which is administered to a human for the treatment of a neurodegenerative disease.
[4] A neurotrophin secretagogue, which comprises as an active ingredient an NO donor.
[5] A BNDF secretagogue, which comprises as an active ingredient an NO donor.

DETAILED DESCRIPTION OF INVENTION

Figure 1A:
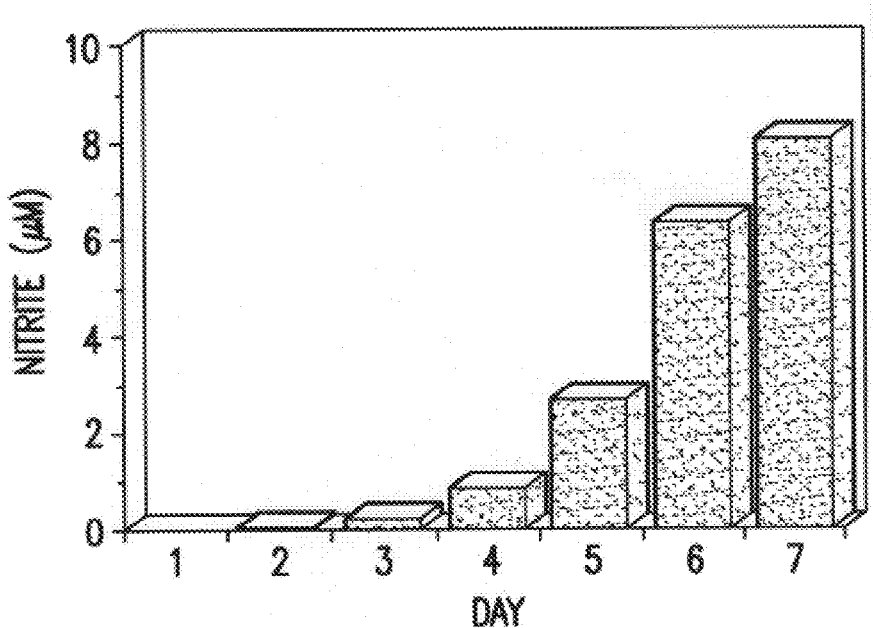
FIG. 1(A) is a graph showing the NO production in a culture of brain neural cells of rat embryo (E18). The axis of ordinates is the concentration of nitrite ($\mu$M) in the culture medium, and the axis of abscissas is the period (day) of the cultivation.

The present invention is illustrated in detail below.
(Definition of Terms)

In the present specification, the "NO donor" is a generic name for medicaments, which can continually release nitric oxide (NO) under biological conditions. Generally, a compound having a nitro group and called nitrate agent or nitro agent is included in this category. The representatives of nitrate agents are sodium nitropruside (SNP), nitroglycerin (NTG), glyceryl trinitrate, isosorbide mononitrate (ISMN), isosorbide dinitrate (ISDN), and molsidomine (Reference 11).

A nitrate agent is considered to react with a thiol group in the living body, and NO is produced from the resulting nitrosothiol, but there are some compounds, which can produce NO without consuming thiol in the living body. They are called "spontaneous NO donor", and many attention have recently been focused upon these compounds as a circulate medicament. S-Nitroso-N-acetyl-DL-penicillamine (SNAP), FK409 (=NOR: Formula 1), NON-Oate (=NOC: Formula 2) or SIN-1 are included in this category (Reference 12).

Formula 1

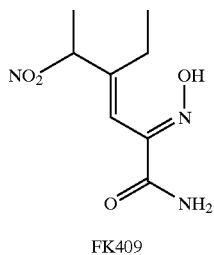

FK409

While the classical nitrate agents such as SNP induce NO resistance due to toxicity of nitrosothiol or by thiol depletion, and thereby they are considered to have difficulties in the clinical use thereof, these spontaneous NO donors such as SNAP, NOR, NOC, etc. show less cytotoxicity and less NO resistance expression than classical nitrate agents, and hence, they can be expected to be useful in the present invention. Some derivatives of the above NO donors may exist, and the present invention also includes these derivatives as long as such derivatives produce NO, and promote the release of neurotrophic factors, in the living body, especially in the central or peripheral nervous system.

Formula 2

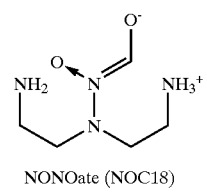

NONOate (NOC18)

Besides, other than SNAP, all of the compounds having a SH group or derivatives prepared by nitrosonizing a protein can act as spontaneous NO donors. Such derivatives are, for example, nitrosonized protein (e.g., S-nitrosoalbumin), nitrocysteine, nitrosoglutathione, nitrosopantothenic acid, and nitrosocaptopril. In the present specification, arginine, which is a biological NOS substrate, is specially included in the NO donor as being a substance promoting the NO synthase (NOS) activity.

Reference 11: Masahiko KINOSHITA, Masayuki TAKAHASHI, IGAKU-NO-AYUMI, special issue, p. 193–196 (1996, 11)

Reference 12: Yoshiki KATAYAMA, IGAKU-NO-AYUMI, special issue, p. 35–40 (1996, 11)

The "neurotrophic factor secretagogue" means a medicament which can promote the secretion of a neurotrophic factor from neural cells when it contacts said neural cells in vivo or in vitro. The neurotrophic factor is a generic name of proteins showing biological activities to maintain the survival and differentiation of neural cells, such as nerve growth factor (NGF), which was found in 1950. The neurotrophic factor includes, for example, a neurotrophin family (References 13 and 14) including brain-derived neurotrophic factor (BDNF), NGF, neurotrophin 3 (NT-3), neurotrophin 4/5 (NT-4/5), and neurotrophin 6 (NT-6), and moreover, glial cell line-derived neurotrophic factor (GDNF), glial cell growth factor (GGF2), central neural cell growth factor (AF-1).

The "neurotrophin" means a neurotrophic factor, which is secreted from the target cells for nerve growth, or from cells extending to the target, or promotes the growth, differentiation, or survival of neurons by autocrine or paracrine, and makes them form a neural circuit (synapse) in the living body. For example, BDNF, NGF, NT-3, NT-4/5, NT-6 are known at the moment, and they are a group of proteins having a high homology of amino acid sequence.

Reference 13: R. M. Lindsay et al., TINS vol. 17, p. 182 (1994)

Reference 14: R. M. Lindsay et al., Phil. Trans. R. Soc. London B vol. 351, p. 365–373 (1996)

The "neurodegenerative disease" is a generic name of diseases associated with deletion or necrosis of neural cells of the central or peripheral nervous system, and the representative ones are, for example, Alzheimer's Disease (AD), Huntington's Disease, Amyotrophic Lateral Sclerosis (ALS), and Parkinson's Disease. Besides, the diabetic or drug-induced peripheral nerve disorders, and retina nerve disorders are also included in the neurodegenerative disease of the present invention.

(Method for Preparation)

The neurotrophic factor secretagogue of the present invention is commercially available or prepared as explained below.

Nitrate Agent

Nitroglycerin (NTG): trade name; Nitroglycerin tablet 0.3 mg (NIPPON KAYAKU CO., LTD.), Myocor spray (Yamanouchi Pharmaceutical Co., Ltd.), Nitroderm TTS (Novartis), etc.

Isosorbide mononitrate (ISMN): trade name; Itorol tablet 10 mg (Yamanouchi Pharmaceutical Co., Ltd.), etc.

Isosorbide dinitrate (ISDN): trade name; Apatya tape (Teikoku), Nitorol tablet 5 mg (Eisai Co., Ltd.), etc.

The above medicaments are commercially available and can clinically be used. In addition, Molsidomine, K channel opener, Nicorandil, and β blocker, Nipuradilol are also medicaments exhibiting the activities as NO donors.

Spontaneous NO Donor

SNAP: SNAP, i.e., S-nitroso-N-acetyl-DL-penicillamine can be obtained from Wako Pure Chemical Industries, Ltd. as a reagent.

NONOate (=NOC): NONOate derivative, i.e., 1-substituted diazen-1-ium-1,2-dioleate can be prepared by the method disclosed in References 15 and 16.

FK409 (=NOR): FK409, i.e., (±)-(E)-4-ethyl-2-[(E)-hydroxyimino]-5-nitro-3-hexeneamide can be prepared by the method disclosed in Reference 17.

SIN-1: SIN-1, i.e., 3-morpholino-sydnoniminium chloride or a derivative thereof can be prepared by the method disclosed in References 18 and 19.

Reference 15: Keefer, L K et al.; Method in Enzymol. 268, 281–293 (1996)

Reference 16: Saavedra, J E et al.; J. Med. Chem. 40, 1947–1950 (1997)

Reference 17: JP-A-59-152366 (=EP 113106, U.S. Pat. No. 4,767,769, Fujisawa Pharmaceutical Co., Ltd.)

Reference 18: German Patent DE 4420523 (Cassella A G)

Reference 19: JP-A-4-244071 (=EP 471232, U.S. Pat. No. 5,166,166, Cassella A G)

(Pharmaceutical Composition)

The above nitrate agents or other NO donors can be formulated into a pharmaceutical composition by combining with conventional pharmaceutical carriers or diluents which are usually used in the pharmaceutical field.

(Administration Route)

The above or other NO donors can be administered to a human by various routes, which are usually employed in the treatment of angina pectoris. When they are administered as a neurotrophic factor secretagogue of the present invention, the dosage thereof can properly be increased as long as they do not show any undesirable effects such as peripheral vasodilating effects or hypotensive effects, or do not induce methemoglobinemia. It is also possible to chronically administer them by using sustained-release formulations.

Nitrate Agents

When nitroglycerin (NTG) is used, the dosage thereof is in the range of 0.5 to 10 mg/day for a patient for oral administration. When it is administered in the form of sublingual tablet or spray preparation, or in the form of patch, it can be administered three times a day, at a dose of 0.3 to 0.6 mg each, and a dose of 2.5 mg each, respectively. When it is administered intravenously, it can be injected continuously in an amount of 20 to 40 $\mu$g/kg. By the excess administration, nitroglycerin may cause hypoglycemia or anemia to patients, and hence, the dosage thereof should be carefully adjusted for a patient with anamnesis (1997-Ed. DRUGS IN JAPAN, ETHICAL DRUGS, published by YAKUGYO JIHO CO., LTD., p. 1066–1074). When isosorbide mononitrate (ISMN) is used, the daily dosage thereof is in the range of 10 to 100 mg for a patient for oral administration, for example, it is administered twice a day at a dose of 20 mg each. When isosorbide dinitrate (ISDN) is used, the daily dosage thereof is in the range of 10 to 100 mg for a patient for oral administration, for example, it is administered three times a day at a dose of 10 mg each (cf. in the above DRUGS IN JAPAN, p. 674–679).

Spontaneous NO Donor

Spontaneous NO donors can be administered either orally, or by intravenous or subcutaneous injection, but since the amount of NO produced by each molecule of spontaneous NO donors such as NONOate, FK409, etc. is higher than that of nitrates agents, the dosage of spontaneous NO donor is in the range of 0.1 to 100 mg/day, preferably in the range of 0.5 to 20 mg/day, for oral administration.

Arginine

Arginine hydrochloride (Arginine 30 g Injection: Roussel Morishita Co., Ltd.-Japan HMR) as an agent for examining pituitary function, and arginine glutamate (Argimate 20 g Injection, Roussel Morishita Co., Ltd.-Japan HMR) as an agent for improving hyperammonemia are commercially available. These agents can be administered either orally or intravenously, and it will exhibit NO production promoting effects by the administration of 0.5 to 20 g/day thereof.

(Toxicity)

The $LD_{50}$ of ISMN, a representative of nitrate agents, is 1050–1550 mg/kg (p.o.), 40 mg/kg (i.v.) in rats in the animal tests. In the oral administration to human, it is estimated that ISDN does not show serious side effects at a dose up to dozens mg per day, and NTG does not show serious side effects at a dose up to several mg per day. It is considered that arginine can be administered at a dose up to 20 g per day of arginine glutamate by intravenous drip, and hence, the toxicity of arginine is quite low.

EXAMPLES

The usefulness of the present invention is illustrated below by Examples.

Example 1

Figure 1B:
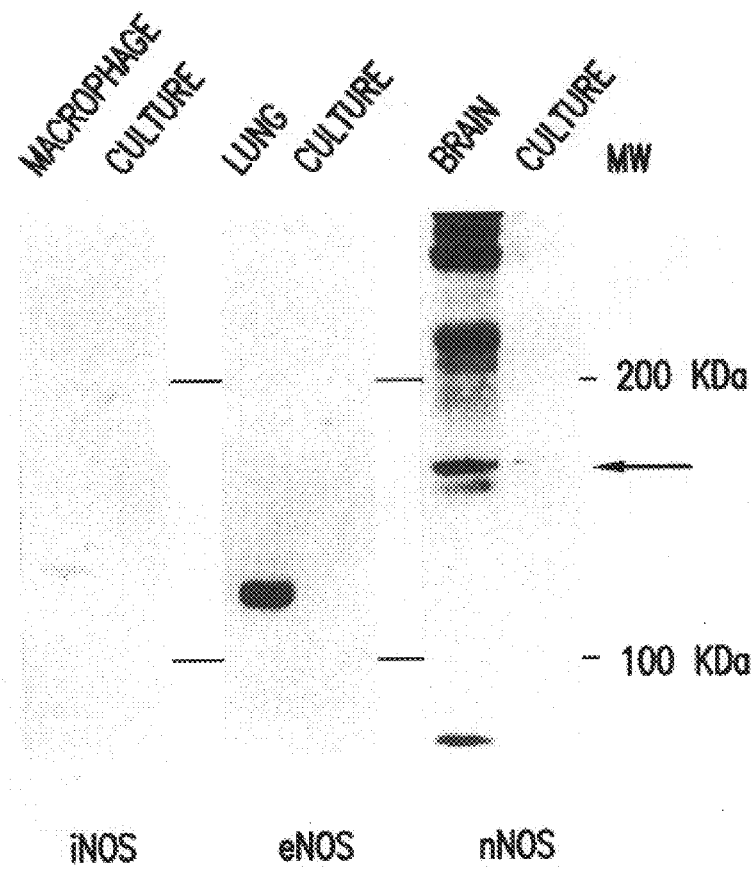
FIG. 1(B) is a photo of the electrophoresis showing the immunochemical detection of NO synthase (nNOS) in the culture of neural cells. The axis of ordinates is the molecular weight (kD), and from the left, the western blots of the sample extracted from the peritoneal macrophage/culture of brain neural cells, the sample extracted from the lung/culture of brain neural cells, and the sample extracted from brain/culture of brain neural cells are indicated, respectively.

Role of Neuronal-Nitrogen Oxide Synthase (nNOS) in NO Production in the Primary Culture of Cerebral Neocortex Neuron The following experiment was done in order to confirm the NO production by neural cells, and to clarify which isozyme of three nitric oxide synthase isozymes (References e1 and e2) (neuronal type; nNOS, endothelial type; eNOS and inducible type; iNOS) is involved with the NO production. The cultured neural cells were prepared by using the neural cells from the cerebral neocortex of rat embryo (E18), and culturing thereof in a serum free medium for 7 days (Reference e3). The supernatant of the culture medium was collected, and the concentration of nitrite was determined, which was used as an index for the total amount of NO production (FIG. 1A). The concentration of nitrite was determined by Griess' method (Reference e4). During the cultivation, the accumulation of nitrite in the supernatant was increased. The expression of NOS in the cultured cells was detected by Western blotting (FIG. 1B). The protein extracted from the cultured cells being electrophoresed on a nitrocellulose membrane was detected by labeling it with 3 anti-NOS antibodies (Transduction Lab., 1/500 to 1000 dilution), treating with peroxidase-labeled anti-IgG antibody, and visualizing by chemical luminescence reaction (ECL kit by Amersham Pharmacia Biotech). In the cultured neural cell sample, the nNOS-like immunoreaction was detected, but eNOS immunoreaction was hardly detected, and further INOS immunoreaction was not detected at all. The product by nNOS immunoreaction as mentioned above has a molecular weight of about 160 kD, which is coincident with that of nNOS as reported in literatures. On the other hand, the definite activity of eNOS and iNOS were observed in the cell extract from lung or peritoneal macrophage, which is quite contrary to the brain neural cells. Besides, when the cultured neural cells were immunohistochemically stained with anti-nNOS antibody (Sigma Chemicals), several percentages of the neural cells were immunoreacted with nNOS, and some of them were simultaneously reacted with anti-trkB antibody as well. From these results, it was suggested that nNOS positive neurons are involved with the NO production mainly in the neocortex culture system as well as can react with BDNF.

Reference e1: Bredt, D S and Snyder, S H; Annu. Rev. Biochem. 63, 175–195 (1994)

Reference e2: Knowles, R G and Moncada S; Biochem. J. 298, 249–258 (1994)

Reference e3: Nawa, H et al.; J. Neurochem. 60, 772–775 (1993)

Reference e4: Green, L C et al.; Anal. Biochem. 126, 131–138 (1982)

Example 2

Effects of NO Donor on the BDNF Expression

Figure 2A:
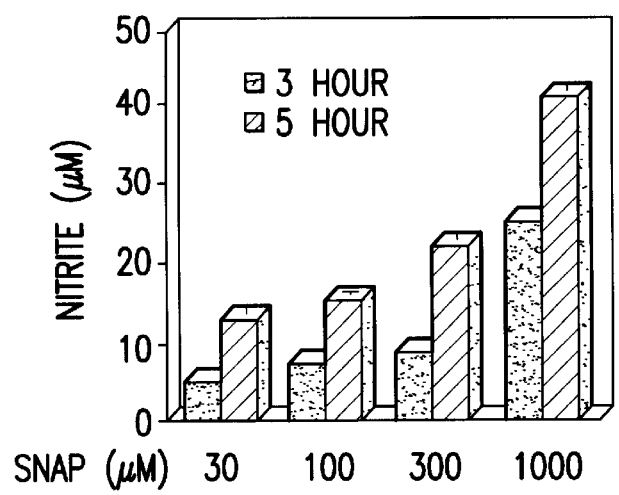
FIG. 2(A) shows the effects of NO donor on the NO production in the cultured neural cell. In the bar graph, the black bar and the diagonal bar show the nitrite level at 3 hours and 5 hours after the SNAP addition, respectively. The axis of ordinates is the nitrite concentration ($\mu$M), and the axis of abscissas is the SNAP concentration ($\mu$M) in the medium.

From the finding that the inhibition of NO synthesis in the cultured brain neural cells increased the expression of BDNF gene, it was clarified that endogenous NO affect the regulation of BDNF gene expression. This finding was further studied by directly adding exogenous NO into the culture system. A spontaneous NO donor, SNAP, was employed in this experiment since SNAP is widely used because the cytotoxicity thereof is weaker than that of other NO donors (Reference e5). SNAP was added to the culture system at various concentrations, and 3 hours and 5 hours thereafter, the BDNF MRNA was determined by quantitative RT-PCR, and the BDNF protein in the cells was determined by EIA, in the same manner as in Example 2. As expected as the above, it was confirmed by determining the nitrite that NO was released from the NO donor (FIG. 2A).

Figure 2B:
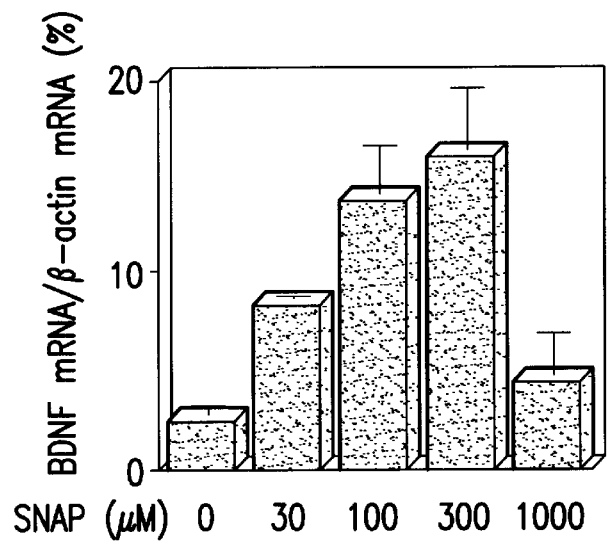
FIG. 2(B) shows the induction of BDNF mRNA by addition of SNAP at various concentrations. In the bar graph, the axis of ordinates is the rates (%) of BDNF mRNA PCR-amplification product to β-actin mRNA amplification product, and the axis of abscissas is the SNAP concentration ($\mu$M) in the medium.
Figure 2C:
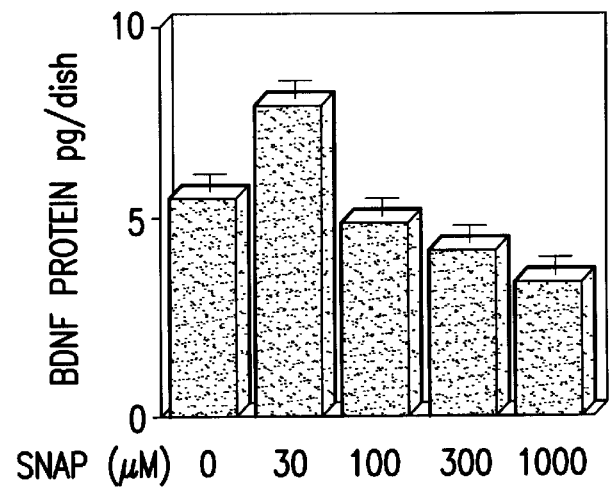
FIG. 2(C) shows the induction of BDNF protein in neural cells by addition of SNAP at various concentrations. In the bar graph, the axis of ordinates is the BDNF protein contents (pg/dish) in the culture dish, and the axis of abscissas is the SNAP concentration ($\mu$M) in the medium.

In this system, SNAP inhibited the expression of BDNF mRNA at a quite high dose (1000 $\mu$M), but it increased dose-dependently the expression of BDNF gene at a lower dose (30 to 300 $\mu$M) (FIG. 2B). It is considered that the inhibition at the high dose is not du to the cytotoxicity of SNAP since there was no change in the growth of cells. Besides, NOR1, which is an NO donor recently developed, also exhibited the same promoting activity. On the other hand, in the EIA which was simultaneously carried out, the BDNF protein in the cells was increased by addition of SNAP only at 30 $\mu$M, which coincides with the results of MRNA assay, but the dose-dependent decrease of BDNF protein was observed by addition of SNAP at a higher dose (FIG. 2C).

The results of the measurement of mRNA indicates that NO at a low concentration stimulates the neurons and makes them to produce BDNF, but NO at a high concentration such as 1000 $\mu$M adversely inhibits the BDNF synthesis. The inconsistence observed in the addition of SNAP at a high dose (100 $\mu$M or more), i.e., the inconsistence between the increase in the BDNF mRNA level and the decrease in the BDNF protein in neural cells, suggests that some factors after the translation process may possibly be changed, for example, the acceleration of BDNF protein release from neural cells.

Reference e5: Garg, U C and Hassid, A: Eur. J. Pharmacol. 237, 243–249 (1993)

Example 3

Effects of an NO Donor on BDNF Release

Figure 3A:
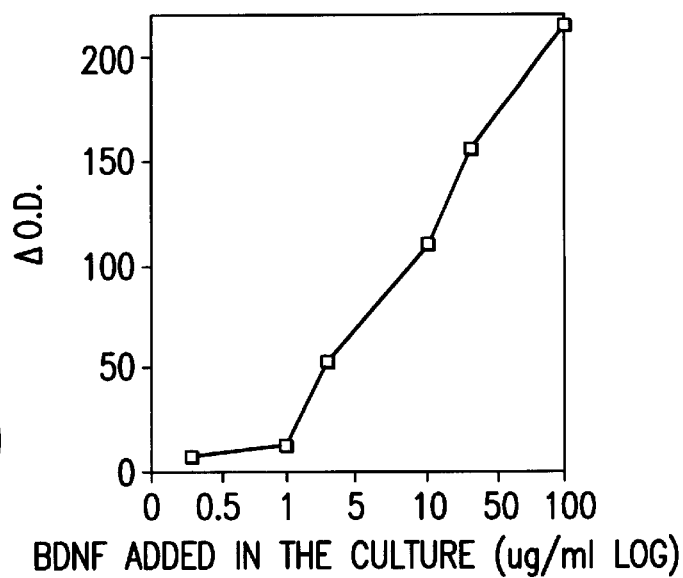
FIG. 3(A) shows the assay of the trkB receptor/BDNF complex by EIA. The graph shows a calibration curve of EIA using the samples to which a prescribed amount of BDNF is added. The axis of ordinates is the absorbance, and the axis of abscissas is the logarithm (ng/ml log) of the concentration of BDNF to be added into the culture.

The effects of an NO donor on the BDNF release were studied in order to clarify the inhibitory effects of SNAP at a high dose on the BDNF protein accumulation. First, the measurement of BDNF concentration in the culture supernatant was tried, but the concentration of BDNF therein was below a detection limitation value of an ordinary EIA, which was considered that the released BDNF immediately combines with the cell surface, even with the trkB receptor. Then, using an anti-pan-trk receptor antibody, a sandwich immunoassay was tried in order to determine the BDNF combined with a trk B receptor on the cell surface. When adding BDNF at a prescribed concentration into the culture system and determining the BDNF therein, there was observed a good correlation between the amount of BDNF to be added and the measured values (FIG. 3A), and hence, the effects of an NO donor on the BDNF release from the neural cells were studied using this newly established assay.

Figure 3B:
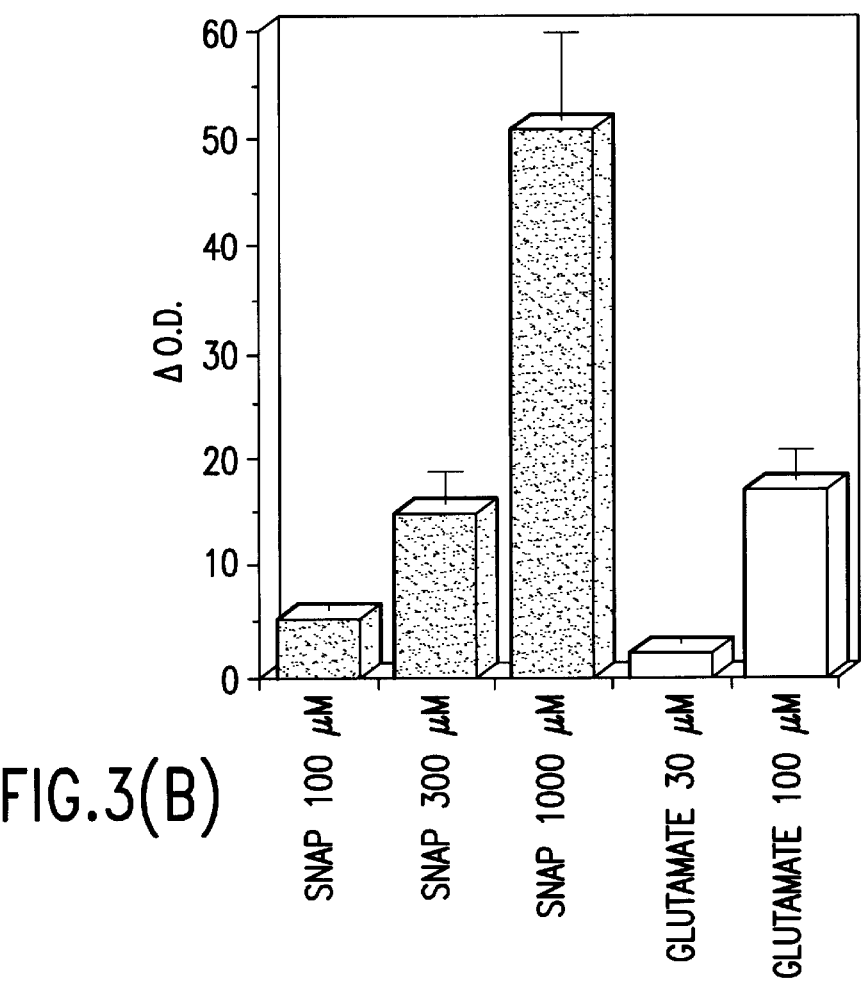
FIG. 3(B) shows the release of BDNF protein from the neural cells by addition of SNAP at various concentrations. In the bar graph, the axis of ordinates is the absorbance, and the axis of abscissas is the concentrations ($\mu$M) of SNAP or glutamic acid in the medium.

From the results, it was confirmed that the NO donor, SNAP, significantly increased the amount of the BDNF-trkB complex at a dose of 100 $\mu$M or more (FIG. 3B). On the other hand, unlike SNAP, the reference compound, glutamic acid (excitatory neurotransmitter), did not show a distinguished BDNF secretion promoting activity to such an extent that it showed a potent BDNF synthesis promoting activity. This finding strongly suggests that NO has a BDNF release promoting activity via a specific mechanism other than its BDNF synthesis promoting activity in the cells. Although NO donor can exhibit the neurotrophic factor release promoting activity at a comparatively high dose thereof, its activity level is more than that of a representative of excitatory neurotransmitters, glutamic acid, and hence, the neurotrophic factor release promoting activity can be a newly found specific biological activity of NO donor.

INDUSTRIAL APPLICABILITY

The medicament of the present invention acts on neural cells, and promotes the secretion of neurotrophic factors such as BDNF therefrom, and hence, it can be expected to exhibit an effect of protecting neural cells or an effect of treating neurodegenerative diseases via said factors.

What is claimed is:

1. A method for promoting the secretion of a neurotrophic factor from neural cells, which comprises treating the neural cells with a nitric oxide donor.

2. The method according to claim 1, which comprises administering a nitric oxide donor to a mammal.

3. The method according to claim 2, wherein the mammal is a human.

4. The method according to any one of claims 1 to 3, wherein the nitric oxide donor is a spontaneous nitric oxide donor.

5. The method according to any one of claims 1 to 3, wherein the neurotrophic factor is a neurotrophin.

6. The method according to any one of claims 1 to 3, wherein the neurotrophic factor is a brain-derived neurotrophic factor.

* * * * *